(12) United States Patent
Browne

(10) Patent No.: US 8,172,776 B2
(45) Date of Patent: May 8, 2012

(54) SYSTEMS AND METHODS FOR DETECTING LABOR CONDITIONS VIA ELECTROMAGNETIC FIELD DISTURBANCES

(76) Inventor: Paul C. Browne, Lexington, SC (US)

( * ) Notice: Subject to any disclaimer, the term of this patent is extended or adjusted under 35 U.S.C. 154(b) by 429 days.

(21) Appl. No.: 12/481,110

(22) Filed: Jun. 9, 2009

(65) Prior Publication Data

US 2010/0312088 A1 Dec. 9, 2010

(51) Int. Cl.
*A61B 5/103* (2006.01)

(52) U.S. Cl. .............................................. 600/588

(58) Field of Classification Search .............. 600/407, 600/409–411, 422, 425, 427, 511, 546, 588, 600/591
See application file for complete search history.

(56) References Cited

U.S. PATENT DOCUMENTS

| | | | |
|---|---|---|---|
| 2,536,527 A | | 1/1951 | Appel |
| 3,409,737 A | | 11/1968 | Settler et al. |
| 3,599,628 A | | 8/1971 | Abbenante |
| 3,703,168 A | | 11/1972 | Frink |
| 3,989,034 A | | 11/1976 | Hojaiban |
| 4,299,234 A | | 11/1981 | Epstein et al. |
| 4,781,200 A | | 11/1988 | Baker |
| 4,984,574 A | | 1/1991 | Goldberg et al. |
| 5,697,369 A | * | 12/1997 | Long et al. ............... 600/407 |
| 5,833,610 A | * | 11/1998 | Yokawa et al. ............ 600/419 |
| 5,935,061 A | * | 8/1999 | Acker et al. ............. 600/304 |
| 6,039,701 A | * | 3/2000 | Sliwa et al. .............. 600/588 |
| 6,418,336 B1 | * | 7/2002 | Kimmlingen et al. ........ 600/410 |
| 6,526,306 B2 | * | 2/2003 | Johnson et al. ............ 600/411 |
| 6,574,497 B1 | * | 6/2003 | Pacetti .................... 600/420 |
| 6,607,486 B1 | | 8/2003 | Watson |
| 6,669,653 B2 | * | 12/2003 | Paltieli .................... 600/588 |
| 6,717,405 B2 | * | 4/2004 | Alsop ..................... 324/306 |
| 6,751,498 B1 | | 6/2004 | Greenberg et al. |
| 7,207,941 B2 | * | 4/2007 | Sharf ..................... 600/438 |
| 2003/0199749 A1 | * | 10/2003 | Lowery et al. ............. 600/409 |
| 2004/0116789 A1 | | 6/2004 | Boas et al. |

FOREIGN PATENT DOCUMENTS

| | | |
|---|---|---|
| CA | 2306530 | 10/2001 |
| GB | 2427692 | 1/2007 |
| GB | 2445454 | 7/2008 |
| WO | 9829035 | 7/1998 |

OTHER PUBLICATIONS

M. Steffen, et al., Non-Contract Monitoring of Heart and Lung Activity by Magnetic Induction Measurement, Acta Polytechnica, vol. 48, No. Mar. 2008, pp. 71-78, Czech Technical University Publishing House.
International Search Report/Written Opinion for PCT/US10/027928 mailed Jun. 4, 2010.

* cited by examiner

*Primary Examiner* — Francis Jaworski
(74) *Attorney, Agent, or Firm* — Sutherland Asbill & Brennan LLP

(57) ABSTRACT

A system may detect a labor condition in a laboring patient. The system may include an electromagnetic field generating unit, an electromagnetic field sensing unit, and a processing unit. The electromagnetic field generating unit may be operable to create an electromagnetic field about the laboring patient. The electromagnetic field sensing unit may be operable to detect a disturbance in the electromagnetic field. The processing unit may be operable to process the disturbance in the electromagnetic field to extract a labor condition.

20 Claims, 4 Drawing Sheets

SYSTEMS AND METHODS FOR DETECTING LABOR CONDITIONS VIA ELECTROMAGNETIC FIELD DISTURBANCES

TECHNICAL FIELD

The present disclosure generally relates to systems and methods for detecting labor conditions, and more particularly relates to systems and methods for detecting labor conditions via electromagnetic field disturbances.

BACKGROUND

Approximately five million children are born each year in the United States alone. Historically, childbirth carried a significant risk of complications, but this risk has substantially abated with the advancement of modern science and technology. For example, monitoring equipment employed during the childbirth process has been instrumental in reducing the risk of childbirth complications. Information used to assess labor includes contractions of muscles such as the maternal uterus and the fetal heart. Such muscular contractions may create an electromagnetic field that can be detected, although typically the electromagnetic fields created by the maternal uterus and fetal heart are relatively weak and are difficult to detect directly.

One type of monitor is a contraction monitor, which monitors the contractions of the uterus throughout the labor process. The contraction monitor provides real-time information regarding the strength and spacing of contractions, which may permit evaluating the progression of the labor and identifying potential complications. Another example is a fetal heart rate monitor, which provides real-time information regarding the rate of the fetal heart beat so that fetal distress may be identified.

One problem with conventional monitoring equipment is that it may not be suited for use with obese patients or other patients having large deposits of fat in the abdominal area. For example, a tocodynomometer is a contraction monitor that detects contractions by measuring changes in the curvature of the abdominal wall. Although highly effective for most patients, the tocodynomometer may not be effective for obese patients, as layers of fat about the abdomen may impede the detection of abdominal wall curvature changes. Another contraction monitor employs electromyographic (EMG) sensors placed on the surface of the patient's abdomen, which measure changes in electrical surface potential caused by uterine contractions. The effectiveness of EMG sensors may be substantially reduced in obese patients, as abdominal fat may increase the distance between the EMG sensors and the uterus, obscuring detection of the contraction signal. Fat also may have a relatively high impedance, distorting the electrical signal associated with the contraction or decreasing its amplitude. These monitors may be especially ineffective at detecting relatively weak contractions in obese patients, such as early labor contractions, Braxton-Hicks contractions, or false labor contractions. Thus, it may be difficult to identify whether an obese patient has truly begun the labor process.

Regarding the monitoring of fetal heart rate, one common monitor employs an EKG electrode attached directly to the head of the fetus within the uterus. Because the electrode is attached internally, the monitor is not suited for use until the membranes of the laboring patient have ruptured. Thus, fetal heart rate may not be monitored until the labor has advanced past the initial stages. For earlier stages of labor, external fetal heart rate monitors have been developed that use technology such as ultrasound. Ultrasound monitors provide a linear beam of ultrasound that is directed at the fetal heart. The maternal abdominal wall may not have a uniform curvilinear surface in an obese patient. If the fetal heart is located near the panniculus of abdominal fat deposits, the ultrasound device may shift position during labor. These position shifts are common in obese patients and may result in periodic inability to detect even the presence of a fetal heart rate during labor. When used on obese patients, both contraction and fetal heart rate monitors suffer from the drawbacks described above. Thus, a need exists for systems and methods of detecting labor conditions as disclosed and claimed below.

SUMMARY

A system may detect a labor condition in a laboring patient. The system may include an electromagnetic field generating unit, an electromagnetic field sensing unit, and a processing unit. The electromagnetic field generating unit may be operable to create an electromagnetic field about the laboring patient. The electromagnetic field sensing unit may be operable to detect a disturbance in the electromagnetic field. The processing unit may be operable to process the disturbance in the electromagnetic field to extract a labor condition.

A method may detect labor conditions via electromagnetic field disturbances. The method may include receiving electromagnetic field information and disturbance information, processing the electromagnetic field information and the disturbance information to identify labor information, and transmitting the labor information to one or more of the following: a display and a database.

Other systems, devices, methods, features, and advantages of the disclosed systems and methods will be apparent or will become apparent to one with skill in the art upon examination of the following figures and detailed description. All such additional systems, devices, methods, features, and advantages are intended to be included within the description and are intended to be protected by the accompanying claims.

BRIEF DESCRIPTION OF THE FIGURES

The present disclosure may be better understood with reference to the following figures. Matching reference numerals designate corresponding parts throughout the figures, and components in the figures are not necessarily to scale.

DETAILED DESCRIPTION

Described below are embodiments of a systems and methods that permit detecting labor conditions via electromagnetic field disturbances. The systems and methods may create an electromagnetic field, may detect a disturbance in the electromagnetic field, and may process the disturbance to extract labor information, such as uterine contraction information and fetal heart rate information, among other labor information. The systems and methods may detect labor conditions with relative specificity and sensitivity, even through excessive layers of abdominal fat that may impede the effectiveness of conventional labor monitors. Thus, the systems and methods may be used with obese patients or other patients having relatively large deposits of abdominal fat. The systems may also be effective in detecting these same labor conditions in patients who are not obese. The systems and methods also may permit detecting labor conditions during relatively early stages of labor, such that labor contractions may be distinguished from Braxton-Hicks contractions associated with false labor. The systems and methods also may be suited for sterility and safety, which may be imperative during the birthing process.

Figure 1:
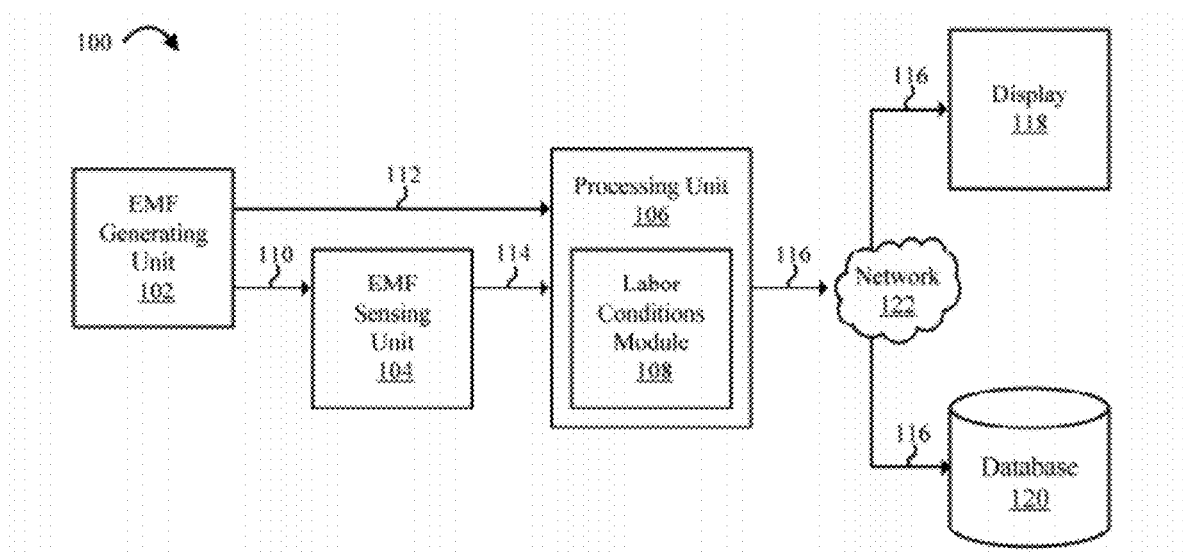
FIG. 1 is a block diagram illustrating an embodiment of a system for detecting labor conditions via electromagnetic field disturbances.

An embodiment of such a system 100 is shown schematically in FIG. 1. As shown, the system 100 generally includes a generating unit 102 operable to generate an electromagnetic field 110, a sensing unit 104 operable to detect a disturbance in the electromagnetic field 110, and a processing unit 106 operable to process disturbances in the electromagnetic field 110 to identify one or more labor conditions.

The EMF generating unit 102 may create an electromagnetic field 110 about a laboring patient, such as in the area of the uterus and associated fetus. An example of the EMF generating unit 102 may include a field generator that causes one or more electromagnets to generate an electromagnetic field 110. The electromagnets may be positioned in a labor bed, in a labor mat, on a side of a labor bed, or in a combination of these and other locations. The EMF generating unit 102 may provide information 112 about the generated electromagnetic field 110 to the processing unit 106, which may facilitate identifying labor conditions.

The EMF sensing unit 104 may detect a disturbance in the electromagnetic field 110 caused by a uterine contraction, a fetal heart beat, another muscular contraction, or combinations thereof. For example, the EMF sensing unit 104 may include a number of electromagnetic sensors. The sensors may be located in a belt device positioned about the laboring patient, in a catheter device inserted into the bladder of the laboring patient, in a probe device inserted into the vagina of the laboring patient, in a probe device inserted into the uterus of the laboring patient, or in a combination of these and other locations. The EMF sensing unit 104 may provide information 114 about disturbances in the electromagnetic field 110 to the processing unit 106, which may facilitate identifying labor conditions.

The processing unit 106 may include a labor conditions module 108, which may process the electromagnetic field information 112 and the disturbance information 114 to extract labor information 116. The labor information 116 may include uterine contraction information, fetal heart beat information, other information, or a combination thereof. The labor information 116 may be transmitted to a display 118 or database 120, such as via a network 122. Thus, labor conditions may be detected in real-time for patients of varying sizes throughout any stage of labor.

Figure 2:
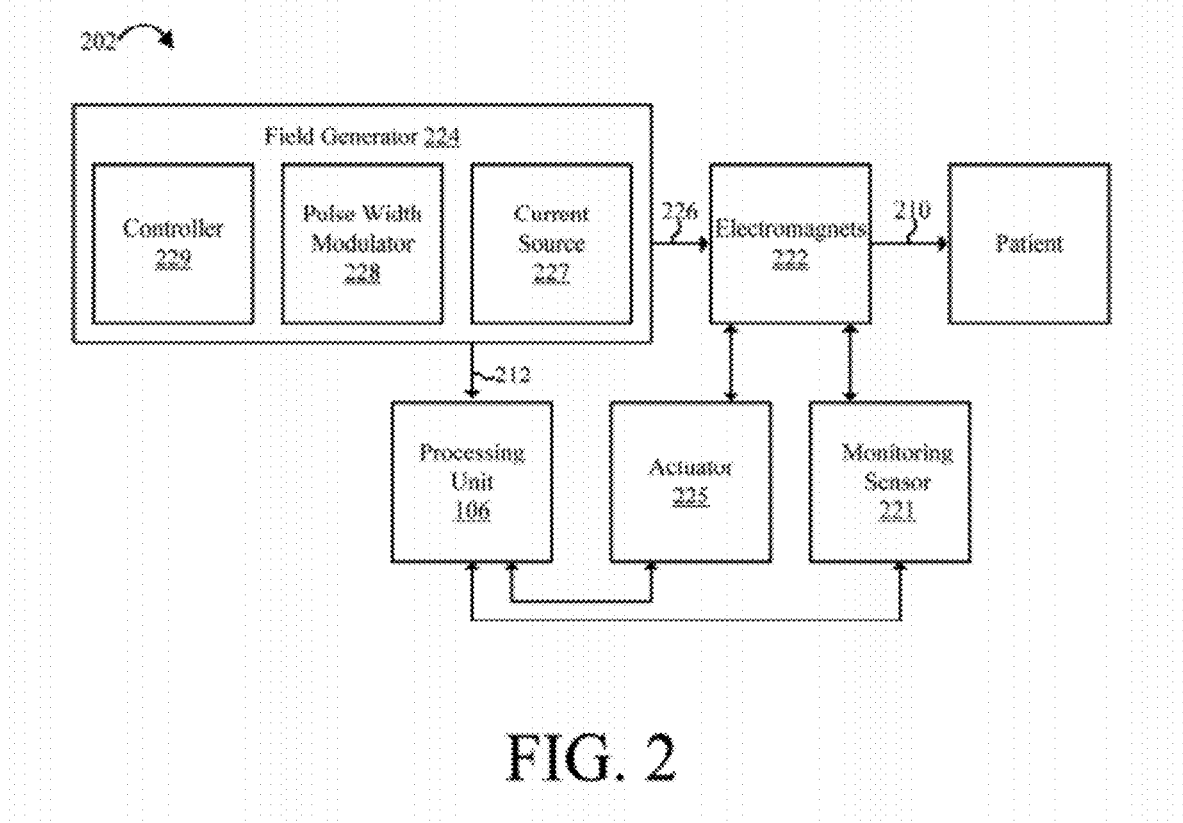
FIG. 2 is a block diagram illustrating an embodiment of a generating unit operable to generate an electromagnetic field about a laboring patient.

FIG. 2 is a block diagram illustrating an embodiment of an EMF generating unit 202. As shown, the EMF generating unit 202 may include one or more electromagnets 222 associated with a field generator 224. The electromagnets 222 may be positioned to produce an electromagnetic field 210 about the patient in the area of the maternal abdomen and fetus. For example, the electromagnets 222 may be positioned beneath the patient, to a side of the patient, inside the patient, or a combination thereof. The field generator 224 may cause the electromagnets 222 to selectively produce the electromagnetic field 210, such as by supplying current to the electromagnets 222 via a field generator line 226. The resulting electromagnetic field 210 may be appropriate for the detection of labor conditions, including maternal contractions and fetal heart beats. For example, the electromagnetic field 210 may be sized to span the area of the maternal abdomen and pelvis. Thus, a maternal contraction or fetal heart beat may disturb the electromagnetic field 210 in a detectable manner. The strength of the electromagnetic field 210 may be sufficient to permit detecting labor conditions without adversely impacting the health of the patient or fetus. For example, the electromagnet field 210 may be a pulsed, extra-low frequency electromagnetic field. Further, each component of the EMF generating unit 202 may be sterilizable, disposal, or a combination thereof.

In embodiments, the field generator 224 may provide current 226 to the electromagnets 222 through a field generator line 226, although other configurations are possible. The current 226 may be a constant current, an alternating current, a pulsed current, or some combination thereof. Depending on the current 226 supplied by the field generator 224, the resulting electromagnetic field 210 may be a constant field, a sinusoidally varying field, a pulsating field, or some combination thereof.

In embodiments, the field generator 224 may convert direct current to pulsed current for supplying to the electromagnets 222. An example of such an embodiment may include a direct current source 227 and a pulse width modulator 228. The pulse width modulator 228 may convert a direct current from the current source 227 to a pulsed current. Thus, the resulting electromagnetic field 210 may be pulsed intermittently, which may lower the overall strength of the electromagnetic field 210 without reducing the peak strength. For example, the electromagnetic field 210 may be a pulsed, extra-low frequency electromagnetic field.

In one example embodiment, the current source 227 may supply a current in the range from about less than one amp to about ten amps. The pulse width modulator 228 may pulse the current at a rate of about one megahertz to about ten megahertz. Upon application of a such a pulsed current, the electromagnets 222 may produce an electromagnetic field 210 of about less than one watt per cubic centimeter to about two watts per cubic centimeter. Such an electromagnetic field 210 may be sufficient to detect labor conditions, even in obese patients during early stages of labor, without harming the laboring patient or fetus.

As an example, an electromagnetic field in the range of one to two watts per cubic centimeter may be sufficient for a patient weighing between about 250 and about 300 pounds. Such an electromagnetic field may be generated using a current on the scale of about one amp and pulsed at about five to ten megahertz. An electromagnetic field of about one watt per cubic centimeter or less may be sufficient for a patient weighing about 150 pounds. Such an electromagnetic field may be generated using a current of less than about one amp and pulsed at about one to five megahertz.

In embodiments, the field generator 224 may be controlled by a controller 229. The controller 229 may control the current 226 in a manner that permits generating an electromagnetic field 210 that is of sufficient strength and penetration depth to detect the desired muscular contractions, yet is safe. For example, the controller 229 may control the frequency and voltage, which may manage the penetration of the electromagnetic field 210 through the patient and thus the amount of energy absorbed. The controller 229 also may operate the field generator 224 within a narrow range of current 226 to ensure a relatively uniform electromagnetic field 210 is generated.

In embodiments, the controller 229 may control the field generator 224 in response to one or more inputs. These inputs may be received from the processing unit 106 or from an input device or other user interface operated by a user, such as a keyboard or mouse. In response to the inputs, the controller 229 may control or provide instructions to one or more of the current source 227 and the pulse width modulator 228. For example, the electromagnetic field 210 may be adjusted in accordance with the weight of the laboring patient, as a relatively stronger electromagnetic field 210 may facilitate detecting contractions in an obese patient. It should be noted that the controller 229 is shown as a component of the field generator 224 for functional purposes. In embodiments, the controller 229 actually may be a component of the processing unit 106, in which case the processing unit 106 may control the field generator 224.

In embodiments, the EMF generating unit 202 may include at least one actuator 225. The actuator 225 may be operable to actuate one or more of the electromagnet 222. For example, the actuator 225 may optimize the orientation or position of the electromagnets 222, such as by rotating or translating the electromagnets 222, to improve the accuracy or resolution of the system. For example, the actuator 225 may adjust the electromagnets 222 in accordance with instructions provided by the processing unit 106, which may be based at least in part on feedback regarding the electromagnetic 210 provided by the EMF sensing unit. Thus, the electromagnetic field 210 may be directed in the desired direction even as the laboring patient moves and rotates.

The EMF generating unit 202 may provide electromagnetic field information 212 to the processing unit 106. For example, the electromagnetic field information 212 may be supplied by the field generator 224 of via the controller 229. The electromagnetic field information 212 may include information about the current supplied by the current source 227, the frequency employed by the pulse width modulator 228, or the overall strength of the generated electromagnetic field 210, among other parameters or combinations thereof. The processing unit 106 may employ the electromagnetic field information 212 to adjust the settings of the controller 229, and to identify labor conditions, as described in further detail below.

In embodiments, the EMF generating unit 202 may also include one or more monitoring sensors 221. The monitoring sensors 221 may be operable to monitor the electromagnets 222. For example, the monitoring sensors 221 may be operable to measure the temperature of one or more of the electromagnets 222 and to communicate the measured temperature to the controller 229 or the processing unit 106. As another example, the monitoring sensors 221 may be operable to measure the current 226 received by the electromagnets 222 and to communicate the measured current to the controller 229 or processing unit 106. In the event an electromagnet 222 becomes overheated or receives excessive current, the controller 229 or processing unit 106 may interrupt the current source 227, the pulse width modulator 228, the field generator supply line 226, or a combination thereof. Thus, the electromagnet 222 may stop receiving current to ensure patient safety.

In embodiments, the electromagnets 222 may be selected, sized, and positioned to create an electromagnetic field 210 that substantially covers the area of the maternal abdomen and fetus. A single relatively large electromagnet 222 may be used, or an array of smaller electromagnets 222 may be used. It may be suitable to use an array of smaller electromagnets 222, as such electromagnets 222 may require relatively less current and may operate at relatively lower temperatures. Some electromagnets 222 may create an electromagnetic field 210 that propagates radially outward through an area that is relatively semi-spherical in shape, while other electromagnets 222 may create an electromagnetic field 210 that propagates relatively linearly through an area that is relatively columnar or beam shaped. It may suitable to use an electromagnet 222 that creates a columnar or beam-shaped electromagnetic field 210, as such electromagnets 222 may require relatively less current and may operate at relatively lower temperatures. Examples configurations for the electromagnets 222 are described below with reference to FIGS. 3-5.

Figure 3:
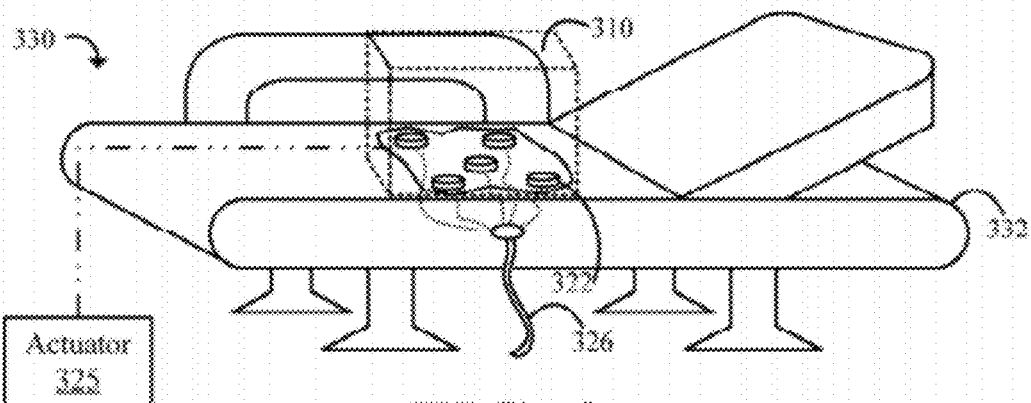
FIG. 3 is a partial cut-away, perspective view of an embodiment of a labor bed that has a number of electromagnets embedded therein.

Specifically, FIG. 3 is a perspective view of a labor bed 330 having a number of electromagnets 322 embedded therein. The labor bed 330 may be any type of labor or hospital bed now known or later developed. The electromagnets 322 may be embedded in a mattress 332 in an area directly below the likely location of the uterus and fetus. Each electromagnet 322 may be in communication with a field generator via a field generator line 326. The electromagnets 322 may form an array. For example, the array may include between about three and about nine relatively smaller electromagnets. Other numbers and configurations may be used herein. Within the array, the electromagnets 322 may be arranged to create individual electromagnetic fields, each of which propagates upward through a relatively columnar area in the pelvic region of the laboring patient. One or more actuators 325 may actuate the electromagnets 322 so as to alter the direction of the electromagnetic field 310. The actuators 325 may actuate the electromagnets 322 individually or as a group. This will allow the electromagnetic field 310 to be focused in the area of interest near the maternal pelvis and fetus. These electromagnetic fields 310 may combine to form an overall electromagnetic field that substantially covers the area of the maternal abdomen and pelvis. Because the overall electromagnetic field 310 may substantially cover the pelvic area, the overall electromagnetic field 310 may be disturbed by muscular activity (contractions) within the area, facilitating detection. Because each individual electromagnet 322 may be relatively small, the electromagnets 322 may operate at relatively lower temperatures and may require less current. Examples of electromagnets 322 that may be used in such an array include Model E-16-260 Tubular Electromagnets manufactured by Magnetic Sensor Systems of Van Nuys, Calif., although any other suitable electromagnet may be used. Such electromagnets 322 may be relatively tubular in structure, resembling a hockey puck, although the electromagnets 322 may also have other shapes, such as square or rectangular shapes. The labor bed 330 may be suited for sterilization and re-use, and thus the labor bed 330 may protect the electromagnets 322 during the birthing process.

Figure 4:
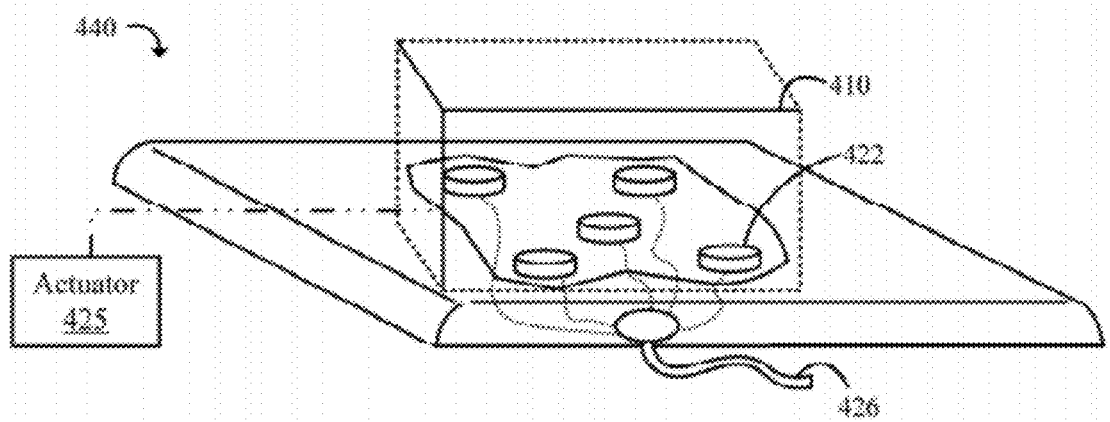
FIG. 4 is a partial cut-away, perspective view of an embodiment of a labor mat that has a number of electromagnets embedded therein.

FIG. 4 is a partial cut-away, plan view a labor mat 440 having a number of electromagnets 422 positioned therein. The labor mat 440 may be positioned under the patient during the birthing process. For example, the labor mat 440 may be placed between the patient and the labor bed. The labor mat 440 may be about the same size as the labor bed, although any size is possible. The labor mat 440 may be manufactured of a biocompatible rubber material, such as a non-latex rubber. An example of such a rubber is ChronoPrene™ Thermoplastic Rubber Elastomer, which is made by AdvanSource Biomaterials Corporation of Wilmington, Mass. Such a labor mat 440 may either be reusable or disposable. In embodiments in which the labor mat 440 is reusable, the labor mat 440 may be sterilizable. A disposable protective covering also may be positioned over the labor mat 440 during the birthing process to keep the labor mat 440 sterile. The cover may be formed from a material that does not attenuate the electromagnetic field, such as a plastic or impermeable cloth material. The labor mat 440 may also include a field generator line 426 that places the electromagnets 422 in communication with a field generator, such as the field generator 224.

Figure 5:
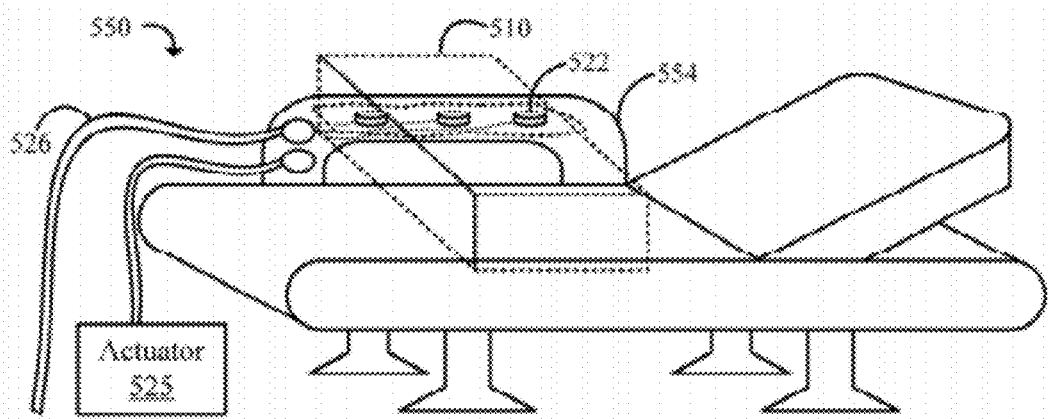
FIG. 5 is a partial cut-away, perspective view of an embodiment of a labor bed that has a number of electromagnets positioned about a lateral side of the labor bed.

FIG. 5 is a perspective view of a labor bed 550 having a number of lateral electromagnets 522 positioned on a side of the bed 550. For example, the lateral electromagnets 522 may be associated with one or more bed rails 554, although other configurations are possible. The lateral electromagnets 522 may be in communication with a field generator, such as the field generator 224, via a field generator line 526. The lateral electromagnets 522 may be provided alone or in combination with electromagnets in a labor bed 330 or mat 440, as described above. In embodiments in which lateral electromagnets 522 are provided, these electromagnets 522 may create an electromagnetic field 510 that is generally transverse in direction to the field created by any electromagnets positioned under the laboring patient. Thus, labor conditions may be detected with increased accuracy, as described in further detail below. The lateral electromagnets 522 also may be movable to accommodate movement of the laboring patient. For example, an actuator 525 may move or rotate the electromagnets 522 in accordance with instructions provided by the processing unit 106, as described below. Thus, the electromagnets 522 may compensate for unanticipated movement or rotation of the laboring patient.

Figure 6:
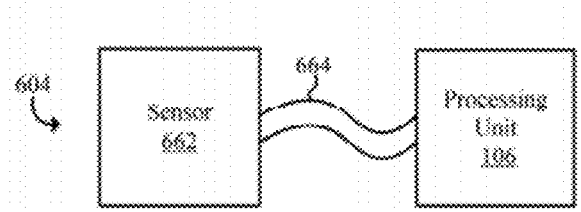
FIG. 6 is a block diagram illustrating an embodiment of a sensing unit operable to detect a disturbance in an electromagnetic field.

Returning to FIG. 1, the system 100 may also include the EMF sensing unit 104, which may be operable to detect a disturbance in the electromagnetic field 110 and to communicate information 114 about the disturbance to the processing unit 106. FIG. 6 is a block diagram illustrating an embodiment of such an EMF sensing unit 604. As shown, the EMF sensing unit 604 may include one or more electromagnetic sensors 662 and a disturbance information line 664. The electromagnetic sensors 662 may be positioned about or within the laboring patient. The electromagnetic sensors 662 may detect disturbances in the electromagnetic field that are caused by muscular contractions in the area through which the electromagnetic field propagates. These muscular contractions may include contractions of the maternal uterus, the maternal bladder, the maternal intestines, the maternal abdominal wall muscles, the fetal muscles, or the fetal heart. The disturbance information line 664 may communicate information about the disturbances from the sensors 662 to the processing unit 106, which may process the disturbance information as described below.

In embodiments, the EMF sensing unit 604 may cooperate with the processing unit 106 to control one or more of the electromagnets. With reference back to FIGS. 2-5, the EMF generating unit may include an actuator operable to adjust the orientation or position of electromagnets. The EMF sensing unit 604 may provide feedback to the processing unit 106 that permits optimizing the orientation or position of the electromagnets to improve the accuracy or resolution of the system. In turn, the processing unit 106 may provide instructions to the actuator, which may adjust the electromagnets accordingly. Thus, the electromagnetic sensors 662 may be able to continuously detect the electromagnetic field generated by electromagnets even as the laboring patient moves and rotates.

Figure 7A:
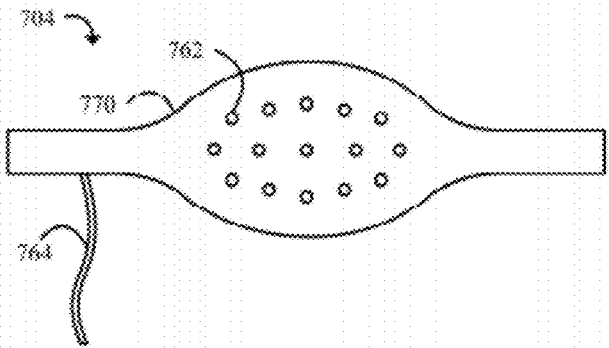
FIG. 7*a* is a plan view of an embodiment of a belt device that is operable to detect a disturbance in an electromagnetic field.
Figure 7B:
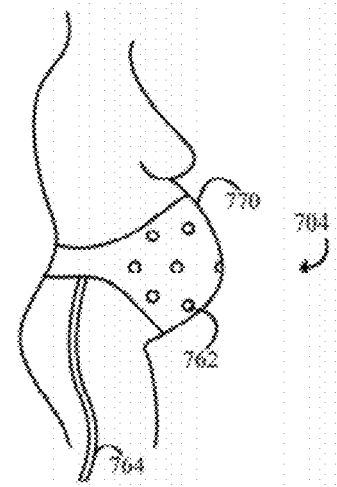
FIG. 7b is a side view of the belt device positioned about the abdomen of a patient.

FIG. 7a is a plan view of an embodiment of an EMF sensing unit 704 that includes a belt device 770, and FIG. 7b is a side view of the belt device 770 positioned about the abdomen of a patient. The belt device 770 may have one or more sensors 762 in communication with a disturbance information line 764 suited for communicating disturbance information to the processing unit 106. The belt device 770 be formed from a biocompatible, pliant, and comfortable material, such as an elastic polymer material or a spandex material. The material may be double-layered so that the sensors 762 may be held out of contact from the abdomen. The circumference of the belt device 770 may depend on the size of the patient. For example, the circumference may be between about 18 inches and about 100 inches, although other circumferences are possible. To ensure a suitably sized belt device 770 is available, the belt device 770 may be made in different sizes, the belt device 770 may be adjustable, or a combination thereof. The belt device 770 also may have a closure or fastener that facilitates attaching the belt device 770 about the abdomen of the patient. Example closures or fasteners include velcro, snaps, buttons, hooks and loops, or other suitable closures. Once the belt device 770 is positioned about the abdomen, the belt device 770 may form to the contour of the laboring patient and the sensors 762 may become appropriately positioned to detect disturbances in the electromagnetic field. After use, the belt device 770 may be either reused or disposed. If reusable, the belt device 770 may be designed for sterilization between uses, or may be covered in a disposable protective cover. Such a protective cover may be formed from a material that does not attenuate the electromagnetic field.

Each sensor 762 may be operable to detect disturbances in the electromagnetic field and to communicate disturbance information to the processing unit 106 through the disturbance information line 764. The disturbance information may be in a variety of forms depending on the configuration of the sensors 762. For example, the sensors 762 may measure the strength of the electromagnetic field and may output a measurable parameter, such as a voltage, in proportion to the measured strength. Example sensors include HMC1042L 2-Axis Magnetic Sensors, which are manufactured by Honeywell International Inc. of Morristown, N.J., although any other suitable sensors may be used.

In embodiments, the belt device 770 may include an array of sensors 762. The sensors 762 may be positioned within the belt device 770 so that when the belt device 770 is attached to the patient, the array covers a suitable portion of the abdomen above the uterus and fetus. As shown in the illustrated embodiment, the array may includes fifteen sensors 762 arranged in three rows, including a top row closest to the head of the patient, a bottom row closest to the foot of the patient, and a middle row between the top and bottom rows. Each row may have five sensors equally spaced across the abdomen. In other embodiments, other configurations are possible. For example, the number of sensors 762 may be adjusted depending on the size of the patient.

Positioning the sensors 762 in an array may facilitate differentiating contractions of the maternal uterus or the fetal heart from other muscular contractions. Each sensor 762 may have a designated location within the belt device 770, and this location may be known by or communicated to the processing unit 106. The sensors may detect the electromagnetic field in more than one axis. Information from the electromagnetic field sensors may include axis information or other information. Information from the sensor array may be used to identify the location, strength, direction of propagation, duration and other information from disturbances in the electromagnetic field. The processing unit 106 may use the designated location of the sensor(s) when processing the disturbance information to identify the labor conditions, as described below.

In other embodiments, one or more internal sensors positioned within the bladder, the vagina, the uterus, or a combination thereof. The internal sensor may be in closer proximity to the uterus, which may increase the sensitivity of detection. Thus, the internal sensor may be relatively smaller than an external sensor without decreasing effectiveness. The internal sensors may be particularly relevant for obese patients, as external sensors positioned about an obese patient may be relatively farther from the uterus and fetus than comparable external sensors positioned about a thinner patient. The internal sensor also may facilitate distinguishing the source of the disturbance in the electromagnetic field, due to the close proximity to the monitored sites. Thus, contractions of the maternal uterus or the fetal heart may be distinguished from contractions associated with other muscular structures, such as the maternal bladder or maternal abdominal wall muscles.

Figure 8:
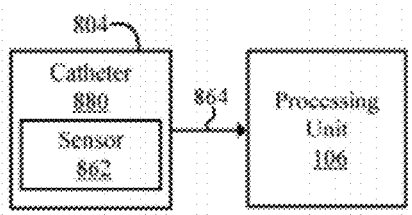
FIG. 8 is a schematic block diagram illustrating an embodiment of a bladder catheter that is operable to detect a disturbance in an electromagnetic field.

FIG. 8 is a block diagram that schematically illustrates an embodiment of an EMF sensing unit 804 for positioning within a bladder of the laboring patient. The EMF sensing unit 804 may include a catheter 880 and one or more internal sensors 862 positioned on the catheter 880. The catheter 880 may be associated with a disturbance information line 864 that communicates disturbance information from the internal sensor 862 to the processing unit 106. Because laboring patients are often catheterized, implanting and removing the internal sensor 862 may not add steps to the labor and delivery process, and because the bladder is in close proximity to the uterus, the internal sensor 862 may be well-positioned to detect contractions of the maternal uterus or fetal heart.

Figure 9:
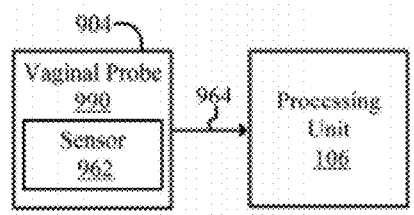
FIG. 9 is a schematic block diagram illustrating an embodiment of a vaginal probe that is operable to detect a disturbance in an electromagnetic field.

FIG. 9 is a block diagram that schematically illustrates an embodiment of an EMF sensing unit 904 for positioning within a vagina or uterus of the laboring patient. The EMF sensing unit 904 may include a vaginal probe 990 and one or more internal sensors 962. The vaginal probe 990 may be associated with an disturbance information line 964 that communicates disturbance information from the internal sensor 962 to the processing unit 106. The probe 990 may extend into the uterus in some embodiments.

Returning to FIG. 1, the system may include a processing unit 106, which may include a labor conditions module or engine 108. The labor conditions module or engine 108 may receive the electromagnetic field information 112 and the disturbance information 114. The labor conditions module or engine 108 may process this information 112, 114 to extract labor information 116. The labor information 116 may include maternal uterine contraction information, fetal heart beat information, or a combination thereof. The labor conditions module or engine 108 may transmit the labor information 116 to a display 118, a database 120, or a combination thereof.

In embodiments, the processing unit 106 may operable to receive one or more user inputs. For example, the processing unit 106 may be in communication with an input device, such as a user interface, that permits a user to enter information such as the weight of the patient, the number of fetuses, or other information. The processing unit 106 may employ such user input information to identify labor information 116.

Figure 10:
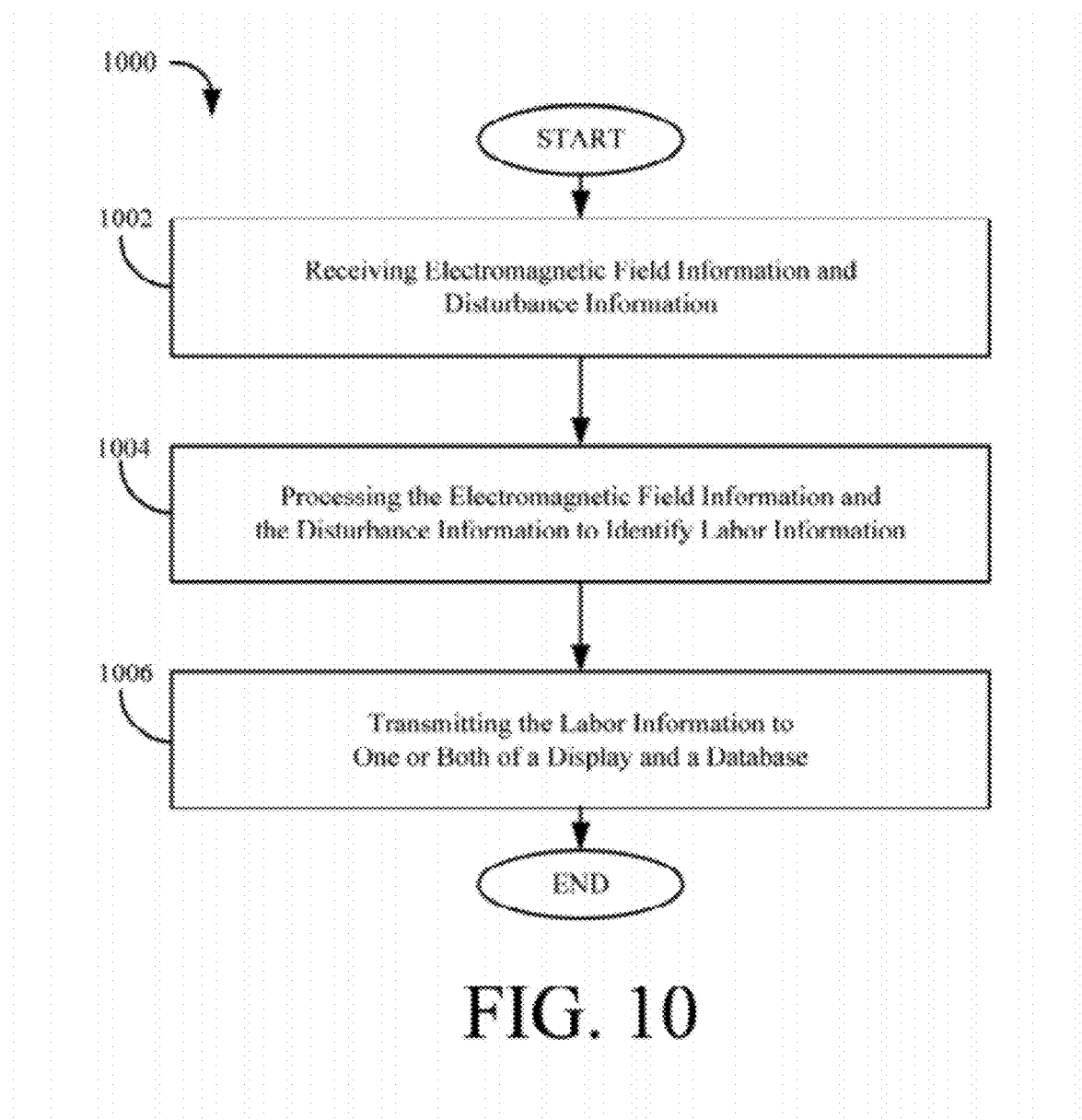
FIG. 10 is a block diagram illustrating an embodiment of a method for detecting labor conditions via electromagnetic field disturbances.

More specifically, the labor conditions module or engine 108 may execute a method 1000 for identifying labor information via electromagnetic field disturbances. An embodiment of such a method is illustrated in FIG. 10.

In block 1002, electromagnetic field information 112 and disturbance information 114 are received. The electromagnetic field information 112 may be received from the EMF generating unit 102, while the disturbance information 114 may be received from the EMF sensing unit 104. The electromagnetic field information 112 may correlate to the electromagnetic field provided to the abdominal area. The disturbance information 114 may correlate to the electromagnetic field detected in the abdominal area. In some embodiments, user input information may also be received.

In block 1004, the electromagnetic field information 112 and the disturbance information 114 may be processed to extract labor information 116. The labor information 116 may include information from contractions of the maternal uterus, the maternal abdominal wall muscles, the maternal bladder, the maternal intestines, the fetal heart, other fetal muscles, other information or a combination thereof. In some embodiments, the user input information may be processed along with the electromagnetic field and disturbance information 112, 114.

In embodiments, processing the electromagnetic field information 112 and the disturbance information 114 in block 1004 may include identifying a cause of a disturbance in the electromagnetic field. When a muscular contraction occurs in the abdominal area, a disturbance in the electromagnetic field may result. The disturbances may be revealed upon comparing the provided electromagnetic field to the detected electromagnetic field, as indicated by the electromagnetic field information 112 and the disturbance information 114 respectively. The disturbances may be further analyzed to identify the cause. For example, the disturbance may have one or more disturbance characteristics that facilitate identifying the cause. The disturbances characteristics may include a magnitude of the disturbance, a duration of the disturbance, a location of the disturbance, a cycling or repetition of the disturbance, or a combination thereof. It is noted that information about the location of the disturbance may be available in embodiments in which the EMF sensing unit 104 includes an array of sensors. In such cases, the disparate locations of the sensors in the array may facilitate obtaining disturbance location information.

The disturbances characteristics may be modeled to identify trends or patterns that indicate the cause. For example, a uterine contraction typically originates at a top of the uterus and propagates downward toward the cervix. The contraction is strongest at the top of the uterus and loses strength as it propagates. A fetal heart beat usually originates from a relatively static location and intermittently repeats at a relatively fast rate. Disturbance characteristics may follow these and other trends or patterns, facilitating identification of the cause of the disturbance.

In embodiments, processing the electromagnetic field information 112 and the disturbance information 114 in block 1004 may further include transforming the information into useful labor information 116. For example, maternal uterine contraction information or a fetal heart beat may be formatted in accordance with conventions understood by a trained medical professional. The transformation may be based in part on an analysis of the disturbance characteristics. For example, a disturbance in the electromagnetic field caused by a uterine contraction may have a magnitude that is roughly proportional to the strength of the contraction, as the uterus is generally relatively large and uniform. Similarly, the duration of the disturbance may correlate to the duration of the contraction, and the location of the disturbance may correlate to the location of the contraction. The correlation of data points such as magnitude, location, duration and other characteristics may help to distinguish labor information such as uterine contractions from other information such as bladder voiding.

In embodiments, processing the information in block 1004 may include filtering disturbances that are not attributable to uterine contractions or fetal heart beats. For example, contractions of the bladder may be filtered, as such contractions are largely irrelevant to the labor and delivery process. In such cases, processing the information may include executing an algorithm or modeling the disturbance information based on one or more of the following: location, magnitude, duration, cycling, and repetition. For example, repetitive events such as fetal heart beat and contractions may be filtered based on repeating patterns such as cycle length, similarity of repeating disturbances and other characteristics of cyclic events.

In block 1006, the labor information 116 may be provided to one or more of a display and a database. The display 118 may be viewable in the labor and delivery room, so that health care professionals attending to the labor may have real-time information about the labor conditions. The database 120 may be an electronic medical records database that stores an electronic medical record of the laboring patient. In embodiments, the labor information 116 may be provided to the display 118 and/or database 120 over a network 122, although the network 122 is not necessary and may be omitted.

In embodiments, the processing unit 106 may be any computer or processor-based device capable of performing the functions described herein. Examples of the processing unit 106 may include a server, a mainframe computer, a personal computer, a desktop computer, a laptop computer, a mobile computer, a handheld portable computer, a digital assistant, a personal digital assistant, a cellular phone, a mobile phone, a smart phone, a pager, a digital tablet, an Internet appliance, any other processor-based device, or combinations thereof. The processing unit 106 may be a single integrated unit as shown, or a number of such units. The processing unit 106 may analyze data independently based on algorithms, computer modeling or other forms of analysis. The processing unit 106 may allow user input such as patient weight, numbers of fetuses and rotation of actuators 220 to optimize the electromagnetic field 110 and adjust the information for the display 118. Manual adjustment of the components of the electromagnetic field generating unit 102 may be permitted. The processing unit 106 may allow user input from devices such as a computer mouse, keyboard, touch-screen display, remote device or other devices. The processing unit 106 may have a user display such as a computer monitor, LED display or other device. The processing unit 106 may also allow voice commands or vocalize settings to the user.

The processing unit 106 may include a processor and a memory. The memory can be coupled to, or in communication with, the processor. The memory may store computer-executable program instructions that, when executed by the processor, cause the processor to perform the steps described herein. In embodiments, computer-executable program instructions stored in a memory of the processing unit 106 may include a labor conditions module 108, which may execute an embodiment of the method 1000. The memory may comprise any computer-readable medium, such as a random-access memory ("RAM"), a read-only memory ("ROM"), or a removable storage device, among others or combinations thereof. The processing unit 106 also may include one or more input/output interfaces ("I/O interfaces") that facilitate communication with other components of the system 100, including user devices such as a keyboard or a mouse, among others.

The processing unit 106 may communicate with the network 122 via a signal, such as a wired communication signal or a wireless frequency signal. The network 122 may be, for example, the Internet, a local area network (LAN), a wide area network (WAN), a public switched telephone network, or a wireless communications network capable of transmitting voice, data, image, and multimedia signals, among others or combinations thereof. It should be noted that the network 122 is provided by way of example. In embodiments, the network 122 may be eliminated completely and the processing unit 106 may communicate with the display 118 or database 120 directly.

The display 118 may include any display suited for displaying data, such as maternal contraction information or fetal heart beat information. Examples of the display 118 can include, but are not limited to, a monitor, a television, or any display in communication with a personal computer or other computing device, an integrated screen or display associated with a personal digital assistant, a cellular phone, a mobile phone, a smart phone, a laptop computer, or other computing device, or a combination of a projecting device and screen, among others. In embodiments, the display 118 may be a single display or multiple displays in a variety of patient care locations. Remote monitoring of the labor information may be made available via the Internet, an Intranet, modem or other telecommunications device. User interfaces may be created using voice commands. Audio displays may be created using vocalizations of data points such as contraction frequency, fetal heart rate or other labor data. Computer-executable program instructions stored in memory may include a display device driver application program, or a display device engine or module. The display device engine or module may be adapted to implement a set of instructions to convert data to a suitable format for displaying. In embodiments, the display 118 may receive a signal from the display device engine associated with the processing unit 106 and may output labor information onto a screen. The computational tasks associated with rendering a graphical image may be performed by the processing unit 106 or by any other component.

The database 120 may be an electronic medical record database, which may store an electronic medical record of the laboring patient. The processing unit 106 may transmit the labor information 116 to the database 120 over the network 122, although other configurations are possible.

Embodiments of the systems and methods described above may facilitate detecting maternal uterine contractions and fetal heat beats. A sensing device suited for detecting an electromagnetic field may be associated with a laboring patient, and the patient may be positioned on a labor bed or mat. The bed or mat may create an electromagnetic field that emanates through the patient, and contractions of the maternal uterus or fetal heat may create disturbances in the electromagnetic field. These disturbances may be detected by the sensing device and processed by the processing device. The processing device may transform the disturbances into useful labor information regarding uterine contractions and/or fetal heart beats. The useful labor information may be displayed on a display or stored in a database.

The systems and methods may permit detecting contractions and fetal heart beats during early stages of labor, when conventional monitors may be ineffective. The systems and methods also may facilitate detecting contractions and fetal heart rate in obese patients. Thus, the treating physician may have access to labor information that is currently not available. The systems and methods may be used alone throughout the entire labor process, or the systems and methods may be combined with conventional monitors in later stages of the labor process, for redundancy.

The systems and methods disclosed herein are described with reference to a laboring human, although the systems and methods may be employed with reference to other animals, mammalian or otherwise. A veterinarian or other suitable professional may adapt the systems and methods described above in accordance with birthing practices for such animals.

It also should be noted that the block diagrams illustrated in the figures may represent functional components, which may be moved, altered, eliminated, or combined with other components when implemented.

While particular embodiments of systems and methods for detecting labor conditions via electromagnetic field disturbances have been disclosed in detail in the foregoing description and figures for purposes of example, those skilled in the art will understand that variations and modifications may be made without departing from the scope of the disclosure. All such variations and modifications are intended to be included within the scope of the present disclosure, as protected by the following claims and the equivalents thereof.

At least the following is claimed:

1. A system for detecting a labor condition in a laboring patient, the system comprising:
    an electromagnetic field generating unit operable to create an electromagnetic field about the laboring patient, the generated electromagnetic field being of relative specificity and sensitivity for patients of varying sizes throughout any stage of labor;
    an electromagnetic field sensing unit operable to detect a disturbance in the generated electromagnetic field due to a labor condition muscular contraction in an area through which the generated electromagnetic field propagates; and
    a processing unit operable to process the disturbance in the generated electromagnetic field due to the labor condition.

2. The system of claim 1, wherein the electromagnetic field generating unit comprises:
    one or more electromagnets; and
    a field generator operable to cause the electromagnets to produce an electromagnetic field.

3. The system of claim 2, wherein the field generator is operable to provide a current to the electromagnets.

4. The system of claim 2, wherein the field generator comprises a direct current source and a pulse width modulator.

5. The system of claim 2, wherein the electromagnets are positioned in one or more of the following: a labor bed, a labor mat, and a bed rail.

6. The system of claim 2, wherein the electromagnetic field generating unit further comprises an actuator operable to move or rotate at least one electromagnet.

7. The system of claim 6, wherein the processing unit is further operable to control the actuator in response to information provided by the electromagnetic field sensing unit.

8. The system of claim 1, wherein the electromagnetic field sensing unit comprises one or more electromagnetic sensors.

9. The system of claim 1, wherein the electromagnetic field sensing unit comprises:
    a belt device adapted for positioning about an abdomen of the laboring patient; and
    one or more electromagnetic sensors positioned within the belt device.

10. The system of claim 1, wherein the electromagnetic field sensing unit comprises:
    a catheter adapted for positioning in a bladder of the laboring patient; and
    one or more electromagnetic sensors associated with the catheter.

11. The system of claim 1, wherein the electromagnetic field sensing unit comprises:
    a probe adapted for positioning in a vagina or a uterus of the laboring patient; and
    one or more electromagnetic sensors associated with the probe.

12. The system of claim 1, wherein the processing unit is further operable to:
    receive electromagnetic field information from the electromagnetic field generating unit; and
    receive disturbance information from the electromagnetic field sensing unit.

13. The system of claim 12, wherein the processing unit is further operable to process the electromagnetic field information and the disturbance information to identify a cause of the disturbance in the electromagnetic field.

14. The system of claim 13, wherein the processing unit is further operable to identify the cause of the disturbance as one or more of the following: a uterine contraction and a fetal heart beat.

15. The system of claim 14, wherein the processing unit is further operable to filter disturbances attributable to other causes.

16. The system of claim 1, wherein the processing unit is operable to extract a labor condition by analyzing one or more disturbance characteristics of the disturbance, the disturbance characteristics including one or more of the following: a magnitude of the disturbance, a location of the disturbance, a duration of the disturbance, and a repetition of the disturbance.

17. The system of claim 1, wherein:
    the system further comprises at least one component selected from the group consisting of: a display and an electronic medical records database; and
    the processing unit is operable to transmit the labor condition to the at least one component.

18. A method of detecting labor conditions via electromagnetic field disturbances, the method comprising:
    generating an electromagnetic field about a laboring patient, the generated electromagnetic field being of relative specificity and sensitivity for patients of varying sizes throughout any stage of labor;
    receiving generated electromagnetic field information and disturbance information due to a labor condition muscular contraction in an area through which the generated electromagnetic field propagates;
    processing the generated electromagnetic field information and the disturbance information to identify labor information; and
    transmitting the labor information to one or more of the following: a display and a database.

19. The method of claim 18, wherein the labor information comprises one or more of the following: uterine contraction information and fetal heart beat information.

20. A system for detecting a labor condition in a laboring patient, the system comprising: an electromagnetic field generating unit operable to create an electromagnetic field about the laboring patient, the generated electromagnetic field being of relative specificity and sensitivity for patients of varying sizes throughout any stage of labor;

an electromagnetic field sensing unit operable to detect a disturbance in the generated electromagnetic field due to a labor condition muscular contraction in an area through which the generated electromagnetic field propagates; and a processing unit operable to:
receive generated electromagnetic field information from the electromagnetic field generating unit;
receive disturbance information from the electromagnetic field sensing unit; and
process the generated electromagnetic field information and the disturbance information to identify a cause of the disturbance as one or more of the following: a uterine contraction and a fetal heart beat.

* * * * *